United States Patent [19]

VandenBerg

[11] Patent Number: Plant 6,938

[45] Date of Patent: Jul. 18, 1989

[54] CHRYSANTHEMUM PLANT NAMED RED REMARKABLE

[75] Inventor: Cornelis P. VandenBerg, Salinas, Calif.

[73] Assignee: Yoder Brothers, Inc., Barberton, Ohio

[21] Appl. No.: 218,225

[22] Filed: Jul. 13, 1988

[51] Int. Cl.[4] ..... A01H 5/00

[52] U.S. Cl. ..... Plt./82

[58] Field of Search ..... Plt./82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Red Remarkable particularly characterized by its flat capitulum form; decorative capitulum type; red ray floret color; diameter across face of capitulum of up to 5.5 cm at maturity; short plant height; spreading and prolific branching pattern; average natural season flower date of September 8 in Salinas, Calif. and October 1 in Hightstown, N.J.; uniform seven week flowering response to short days; and durable, uniform performance in outside fall flowerings and in spring small pot flowering programs.

3 Drawing Sheets

The present invention comprises a new and distinct cultivar of Chrysanthemum, botanically known as *Dendranthema grandiflora,* and referred to by the cultivar name Red Remarkable.

Red Remarkable, identified as 79M33A02, is a product of a mutation induction program which had the objective of creating new Chrysanthemum cultivars that would expand the color range of an existing cultivar while retaining all other traits.

Red Remarkable was discovered and selected by Cornelis P. VandenBerg on Sept. 27, 1984 in a controlled environment in Salinas, Calif. as one flowering plant within a flowering block established as rooted cuttings from stock plants which had been exposed as unrooted cuttings to an X-ray source of 1750 rads. The irradiated parent was the cultivar identified as Remarkable, disclosed in U.S. Plant Pat. No. 5,447.

The first act of asexual reproduction of Red Remarkable was accomplished when vegetative cuttings were taken from the initial selection in December 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Red Remarkable are firmly fixed and are retained through successive generations of asexual reproduction.

Red Remarkable has not been observed under all possible environmental conditions. The phenotype may vary significantly with variations in environment such as temperature, light intensity, and daylength.

The following observations, measurements and comparisons describe plants grown in Salinas, Calif., and Leamington, Canada under greenhouse conditions which approximate those generally used in commercial greenhouse practice.

The following traits have been repeatedly observed and are determined to be basic characteristics of Red Remarkable, which, in combination, distinguish this Chrysanthemum as a new and distinct cultivar:

1. Flat capitulum form.
2. Decorative capitulum type.
3. Red ray floret color.

4. Diameter across face of capitulum up to 5.5 cm at maturity.
5. Short plant height.
6. Spreading and prolific branching pattern.
7. Average natural season flower date of September 8 in Salinas, Calif. and October 1 in Hightstown, N.J.
8. Uniform seven week flowering response to short days in photoperiodic controlled flowering programs.
9. Durable, uniform performance in outside fall flowerings and in spring small pot flowering programs.

The accompanying photographic drawings show typical inflorescence and leaf characteristics of Red Remarkable, with the colors being as nearly true as possible with illustrations of this type.

Sheet 1 is a color photograph of Red Remarkable grown as a pinched pot mum grown in a 10 cm pot.

Sheet 2 is a black and white photograph of three views of the inflorescence of Red Remarkable.

Sheet 3 is a black and white photograph showing the upper and under sides of the leaves of Red Remarkable at three stages of development (mature, intermediate and immature).

Of the commercial cultivars known to the inventor, the most similar in comparison to Red Remarkable is the parent cultivar Remarkable. All traits of Red Remarkable are similar to those of Remarkable, except the color of ray florets. The color of the ray florets of Red Remarkable is a darker red with a better color retention under high temperatures when compared to Remarkable.

In the following description, color references are made to The Royal Horticultural Society Colour Chart (RHS). The color values were determined on plant material grown as a pinched disbudded pot mum in Salinas, Calif. on Apr. 5, 1988. It should be noted that there is no color panel in RHS which accurately depicts true flower color. The color values appearing below for ray floret color are the closest values available but are brighter than the true ray floret color.

Classification:

*Botanical.*—*Dendranthema grandiflora,* cv Red Remarkable.

*Commercial.*—Decorative spray pot mum and garden mum.

INFLORESCENCE

A. Capitulum:
*Form.*—Flat.
*Type.*—Decorative.
*Diameter across face.*—Up to 5.5 cm at maturity.

B. Corolla of ray florets:
*Color (general tonality from a distance of three meters).*—Red.
*Color (upper surface).*—Not as bright as 42-B.
*Color (under surface).*—171D, streaked with 171A.
*Shape.*—Straight. Crossection concave, oblong.

C. Corolla of disc florets:
*Color (mature).*—12A.
*Color (immature).*—2A. Very few disc florets, covered by inner rows of ray florets. Under certain conditions disc florets are not present.

D. Reproductive organs:
*Androecium.*—Present on disc florets only, very few; scant pollen.
*Gynoecium.*—Present on both ray and disc florets.

PLANT

A. General appearance:
*Height.*—Short.
*Branching pattern.*—Spreading and prolific.

B. Foliage:
*Color (upper surface).*—147A.
*Color (under surface).*—147B.
*Shape.*—Lobed and serrated.

I claim:

1. A new and distinct Chrysanthemum plant named Red Remarkable, as described and illustrated.

* * * * *

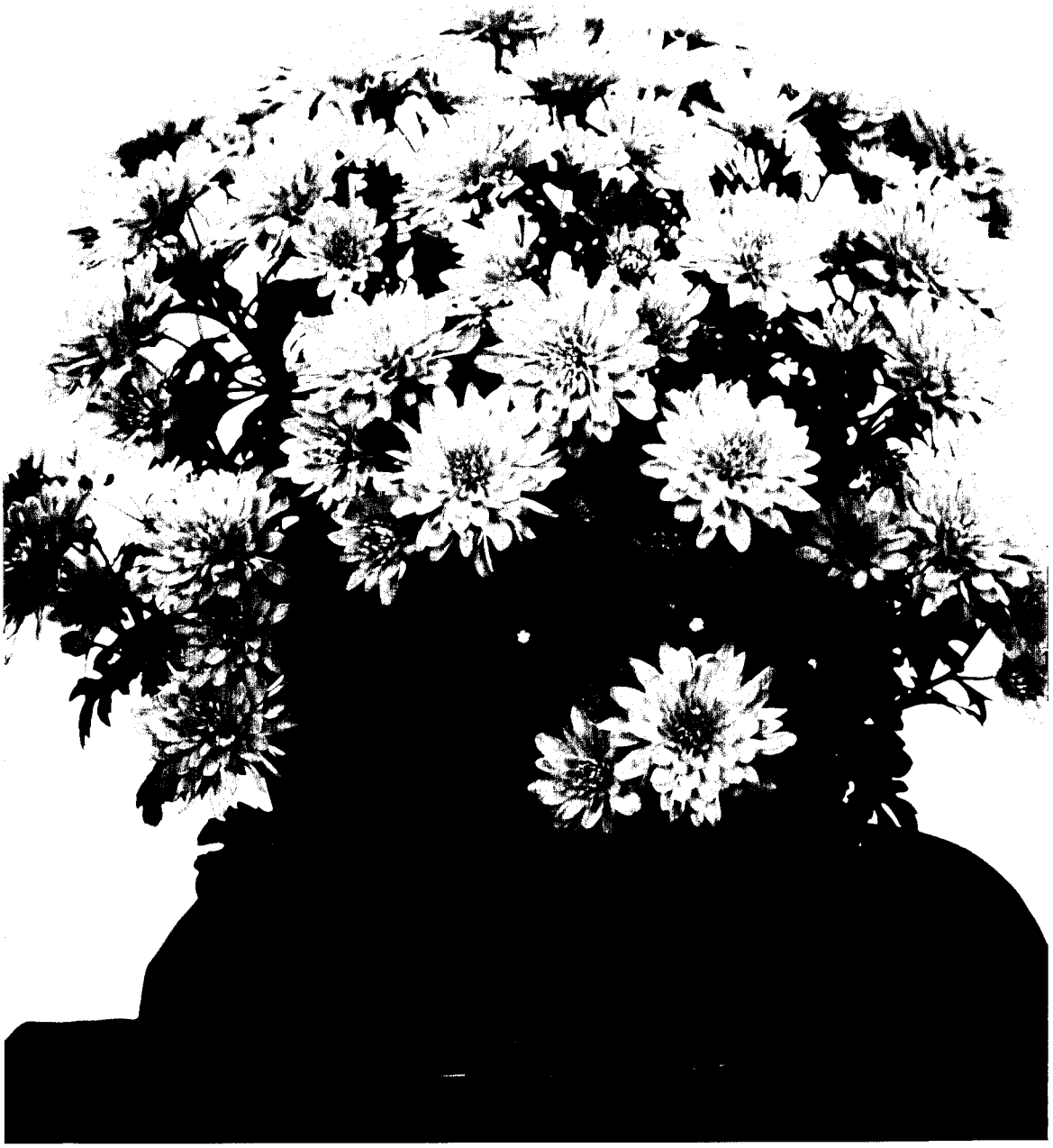

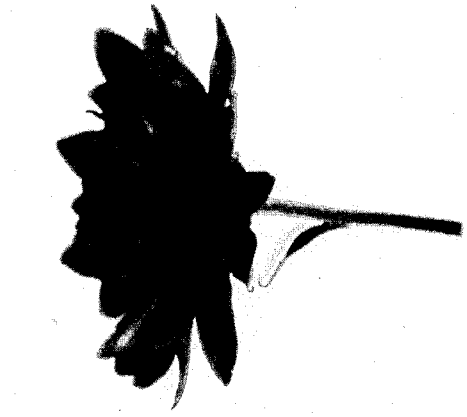
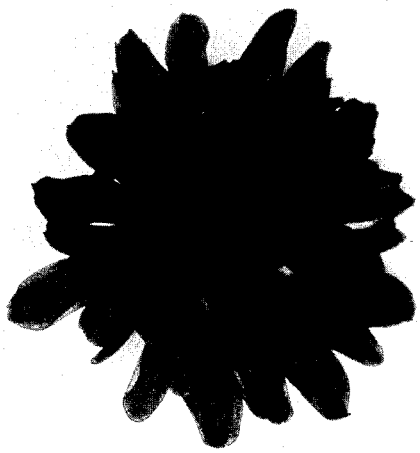
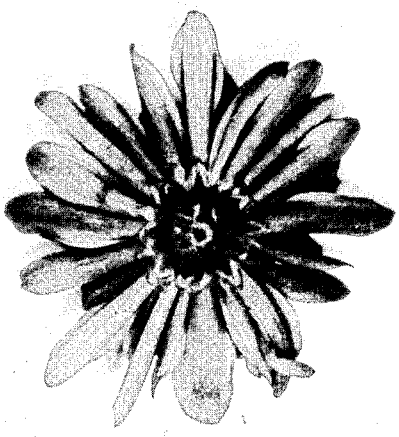

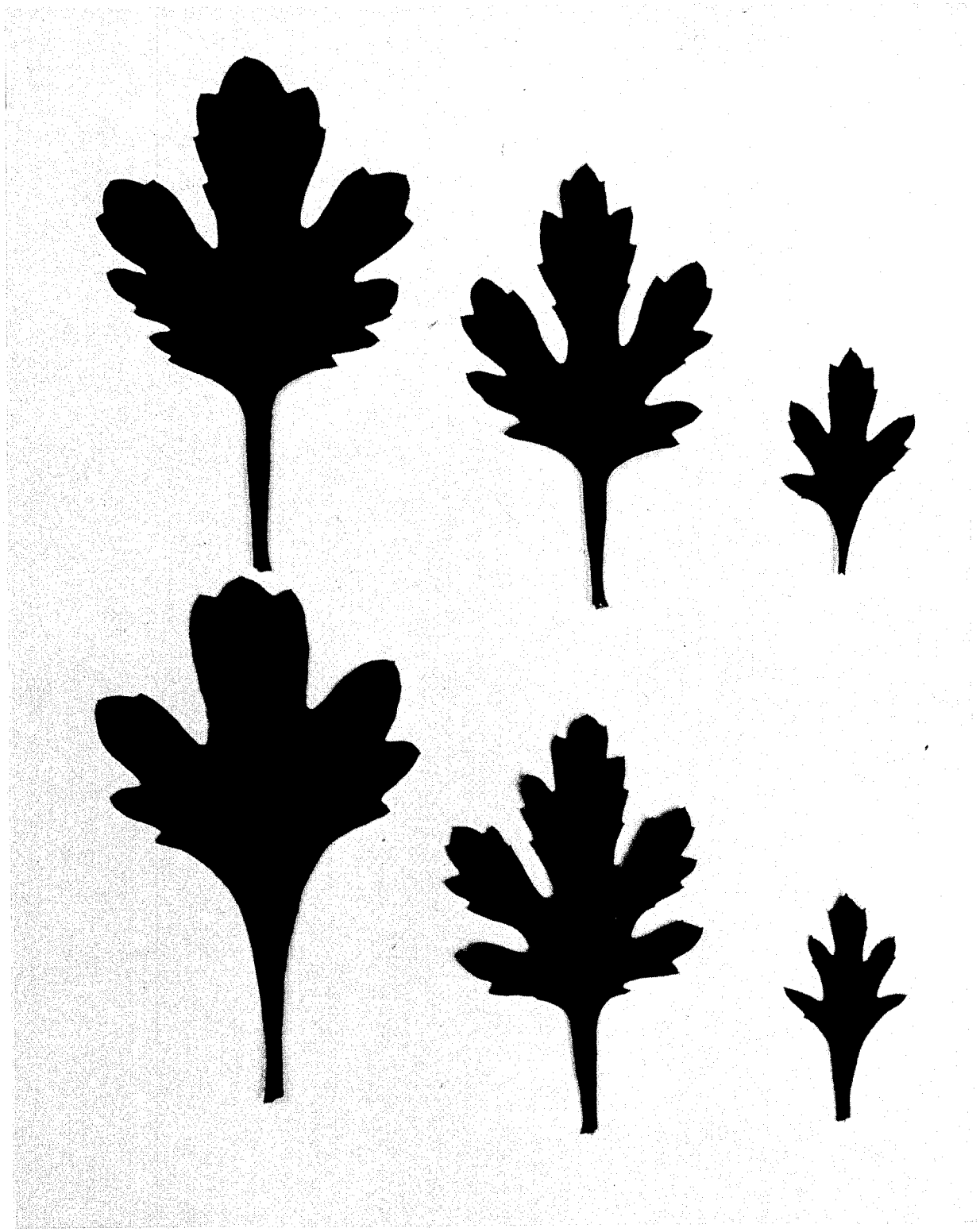

UNITED STATES PATENT AND TRADEMARK OFFICE

CERTIFICATE OF CORRECTION

PATENT NO. : Plant 6,938
DATED : July 18, 1989
INVENTOR(S) : Cornelis P. VandenBerg It is certified that error appears in the above—identified patent and that said Letters Patent is hereby corrected as shown below:

Column 3, line 11, "42-B" should be --42A-B--.

Signed and Sealed this

Twenty-eighth Day of April, 1992

*Attest:*

HARRY F. MANBECK, JR.

*Attesting Officer*

*Commissioner of Patents and Trademarks*